United States Patent [19]

Potier et al.

[11] 4,347,249
[45] Aug. 31, 1982

[54] CLASS OF SECO BIS-INDOLIC COMPOUNDS WHICH CAN BE USED AS DRUGS AND A PROCESS FOR THE PREPARATION THEREOF

[75] Inventors: Pierre Potier, Bois d'Arcy; Nicole Langlois; Yves Langlois, both of Bures-sur-Yvette; Ratremaniaina Z. Andriamialisoa, Les Ulis; Pierre Mangeney, Paris, all of France

[73] Assignee: Agence Nationale de Valorisation de la Recherche (ANVAR), France

[21] Appl. No.: 167,377

[22] Filed: Jul. 9, 1980

[30] Foreign Application Priority Data

Jul. 17, 1979 [FR] France ............................... 79 18453

[51] Int. Cl.$^3$ .................. A61K 31/475; C07D 519/04
[52] U.S. Cl. .............................. 424/262; 260/244.4; 546/51
[58] Field of Search ........................ 546/51; 424/262

[56] References Cited

U.S. PATENT DOCUMENTS 4,122,081  10/1978  Thompson et al. .............. 260/244.4
4,144,237   3/1979  Kutney ............................. 260/244.4

FOREIGN PATENT DOCUMENTS 1095833  3/1965  United Kingdom.
1102224  3/1965  United Kingdom.

OTHER PUBLICATIONS

Kutney et al., Heterocycles, vol. 9, No. 4, pp. 493–497 (1978).
Kutney et al., Heterocycles, vol. 11, pp. 69–73 (1978).
Potier et al., C. R. Seances Soc. Biol. Ses. Fil., vol. 173, No. 2, pp. 414–424 (1979).
Mangeney et al., J. Org. Chem., vol. 44, No. 22, pp. 3765–3768, (10/26/79).
Mangeney et al., Tetrahedron, vol. 35, No. 15, pp. 2175–2179 (10/13/79).

Primary Examiner—Donald G. Daus
Assistant Examiner—Diana G. Rivers
Attorney, Agent, or Firm—Maky, Renner, Otto & Boisselle

[57] ABSTRACT

The invention relates to new chemical compounds. They are compounds corresponding to formula Ia.

in which: $R'_3$ represents a hydrogen atom or a hydroxy radical; $R'_5$ represents a hydrogen atom or a hydroxy radical; or $R'_3$ and $R'_5$ together represent an epoxy bridge or a double bond; $R''_5$ represents a hydrogen atom or an ethyl radical; $R'_7$ and $R'_8$ are the same or different and represent a hydrogen atom or a methyl, hydroxymethylene, alkoxymethylene, aryloxymethylene, aminomethylene, monoalkyl or dialkyl aminomethylene, acylmethylene, arylaminomethylene, hydroxyethyl aminomethylene, alkylthiomethylene, aryloxythiomethylene or cyanomethylene radical; $R_1$ represents a hydrogen atom or an alkyl, formyl or acyl radical: $R_2$ represents a hydrogen atom or an alkoxy radical; $R_7$ represents an alkanoyloxy radical, the broken line representing an optional double bond.

These compounds can be used as drugs.

18 Claims, No Drawings

CLASS OF SECO BIS-INDOLIC COMPOUNDS WHICH CAN BE USED AS DRUGS AND A PROCESS FOR THE PREPARATION THEREOF

FIELD OF THE INVENTION

The present invention relates to new bis-indolic compounds and a process for the preparation of these compounds as well as to their application as drugs.

DESCRIPTION OF THE PRIOR ART

It has been known for some time that natural alkaloids such as vinblastine or vincristine which correspond to the formula:

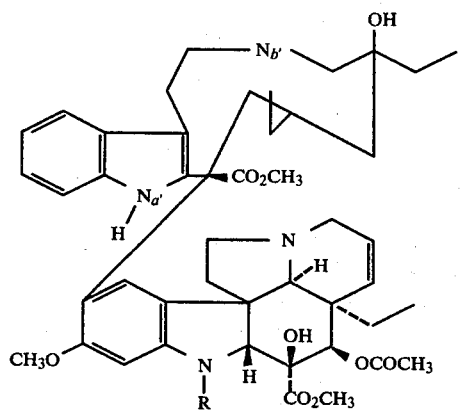

($R=CH_3$: vinblastine, $R=CHO$; vincristine) and which can be isolated from several species of Catharanthus, in particular C. roseus, have anti-tumoral properties. As these alkaloids are only present in a very small quantity in plants, attempts have been made to prepare more active derivatives of these compounds, cf. BSM 5487 M, 6668 M, French Pat. No. 222 18 095. French Pat. Nos. 74 43221 and 77 11081 also propose synthesis processes which open the way to new compounds which have an identical structure but are substituted in different ways.

However, the compounds propose in the prior art always maintained the basic skeleton of vinblastine.

SUMMARY OF THE INVENTION

The present invention relates to new chemical compounds having, in particular, an anti-tumoral activity and exhibiting a different basic skeleton from that of vinblastine.

These are compounds corresponding to the formula:

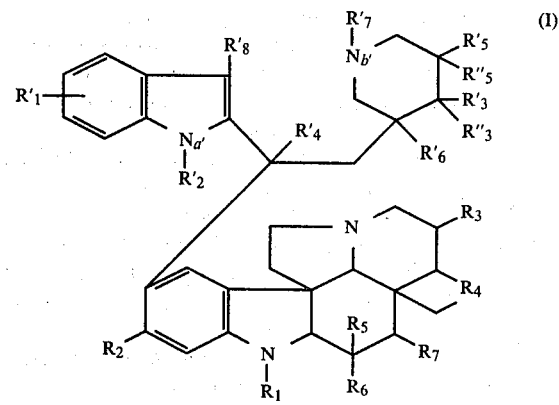

in which:
$R'_1$ represents a hydrogen atom or an alkoxy, acyl, formyl or halogenoacyl radical,
$R'_2$ represents a hydrogen atom or an alkyl radical,
$R'_3$ and $R''_3$ are the same or different and represent a hydrogen atom or a hydroxyl or alkanoyloxy radical, or $R'_3$ and $R''_3$ together form a carbonyl group, or $R'_3$ and $R'_5$ together form an epoxy bridge or a double bond,
$R'_4$ represents a hydrogen atom or an alkyloxycarbonyl, hydroxymethyl, alkanoyloxymethyl or acetamido radical,
$R'_5$ and $R''_5$ are the same or different and represent a hydrogen atom or a hydroxyl, alkanoyloxy, ethyl or 2-hydroxyethyl radical,
$R'_6$ represents a hydrogen atom or an ethyl, 2-hydroxyethyl or acetyl radical,
$R'_7$ and $R'_8$ represent a hydrogen atom or a methyl, alkoxymethylene, arloxymethylene, hydroxymethylene, aminomethylene, monoalkyl or dialkyl aminomethylene, arylaminomethylene, hydroxyethyl aminomethylene, alkyl thiomethylene, aryl thiomethylene, cyanomethylene or acylmethylene radical
$R_1$ represents a hydrogen atom or an alkyl, formyl or acyl radical,
$R_2$ represents a hydrogen atom or an alkoxy radical,
$R_3$ represents a hydrogen atom or a hydroxyl or alkanoyloxy radical, or $R_3$ and $R_4$ together form an epoxy bridge or a double bond,
$R_4$ represents a hydrogen atom or a hydroxyl, alkanoyloxy radical or $R_4$ and $R_5$ together form an epoxy bridge,
$R_6$ represents an alkyloxycarbonyl, hydrazido, acetamido, hydroxymethyl or alkanoyloxymethyl radical,
$R_5$ and $R_7$ represent a hydrogen atom or a hydroxyl or alkanoyloxy radical,
as well as their acid addition salts and their quaternary ammonium salts.

DETAILED DESCRIPTION OF THE INVENTION

The alkyl radicals mentioned in the present description are preferably straight-chained or branched lower alkyl radicals having from 1 to 5 carbon atoms such as the methyl and ethyl radicals.

The alkoxy radicals mentioned in the present description are preferably lower alkoxy radicals corresponding to the above-mentioned alkyl radicals, that is to say, for example, the methoxy and ethoxy radicals.

The acyl radicals mentioned in the present description are, for example, the acyl radicals originating from saturated or unsaturated lower carboxylic acids, such as the acetyl or propionyl radicals.

Similarly, the alkanoyloxy radicals are preferably the radicals corresponding to the above-mentioned acyl radicals, such as the acetyloxy radical.

The alkyloxycarbonyl radicals are preferably radicals in which the alkyl portion corresponds to the preferred definition given above, for example, the methoxycarbonyl radical.

The aryl radicals mentioned in the present description are preferably monocyclic aryl radicals containing five or six atoms in the ring and, in particular, the phenyl radical.

From among the addition salts and the quaternary ammonium salts, the non-toxic, pharmaceutically acceptable salts such as the salts of inorganic acids like hydrochloric acid, or of organic acids like acetic acid, propionic acid, succinic acid or tartaric acid, will preferably be prepared.

The invention relates more particularly to the compounds corresponding to formula Ia:

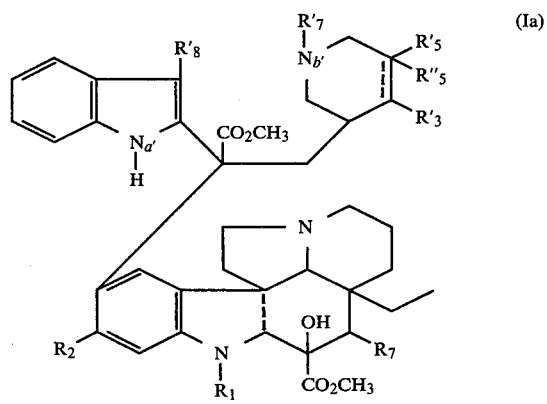

in which:
R'$_3$ represents a hydrogen atom or a hydroxy radical,
R'$_5$ represents a hydrogen atom or a hydroxy radical, or
R'$_3$ and R'$_5$ together represent an epoxy bridge or a double bond,
R"$_5$ represents a hydrogen atom or an ethyl radical,
R'$_7$ and R'$_8$ represent a hydrogen atom or a methyl, alkoxymethylene, aryloxymethylene, monoalkyl or dialkyl aminomethylene, arylaminomethylene, hydroxyethylaminomethylene, alkyl thiomethylene, arylthiomethylene, cyanomethylene or acylmethylene radical,
R$_1$ represents a hydrogen atom, an alkyl, formyl or acyl radical,
R$_2$ represents a hydrogen atom or a methoxy radical,
R$_7$ represents an alkanyloxyl radical, the broken line representing an optional double bond,
as well as the corresponding salts.

The present invention also relates to a process A for the preparation of the compound corresponding to formula I, characterised in that:
(a) a compound corresponding to formula II

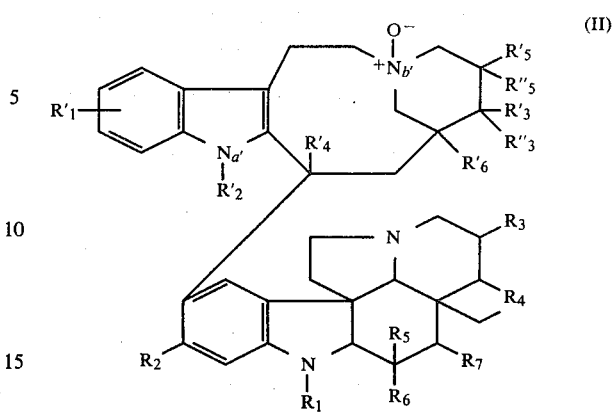

in which the substituents have the meaning given above, is reacted in the presence of an immonium ion-forming reagent, and
(b) the immonium ion obtained is treated with one or more nucleophilic reagents and the compound corresponding to formula I is separated.

Suitable immonium ion-forming agents preferably include the haides, anhydrides or salts of organic or inorganic acids, in particular of carboxylic acids which have been halogenated (in particular fluorinated) or not halogenated.

The immonium ion-forming reagents include, for example, acetic or trifluoroacetic acid anhydride.

Stage (a) is preferably carried out in an anhydrous organic solvent such as a chlorinated solvent, methylene chloride, dichloroethane or chloroform.

Reaction (a) is preferably carried out at a temperature of between $-5°$ C. and $+5°$ C., for example at $0°$ C.

Stage (b) is preferably carried out in a solvent, in particular an organic solvent such as methanol, ethanol, tetrahydrofuran, dioxan, dimethylformamide, dimethylsulphoxide, hexamethylphosphorotriamide or acetonitrile, chloroform or dichloromethane.

Stage (b) can be carried out at ambient temperature.

To prepare the compounds corresponding to formula I in which R'$_7$ and R'$_8$ are of the form R'$_7$=—CH$_2$—R"$_7$ and R'$_8$=—CH$_2$—R"$_8$, one or more nucleophilic reagents which fix the R"$_7$ and R"$_8$ radicals in the 5' and 6' position of the immonium ion will be used. (The preparation of these immonium ions is also described in French Patent Application No. 78 24569 in the name of the applicants.)

The solvent used in stage (b) can itself be a nucleophilic reagent such as methanol or ethanol for fixing the corresponding R"$_7$ and/or R"$_8$ alkoxy radicals.

Other suitable nucleophilic reagents include the hydride ions obtained by the action of an alkaline borohydride, the cyanide ions, the thiolate, thiophenate or phenate ions, an amine or ammonia or a carboxylic acid, depending on the type of substituent which is to be fixed.

If one of the substituents R'$_7$ and/or R'$_8$ is the hydrogen atom, the immonium ion is treated in solution by an alkaline agent such as sodium carbonate in water.

If a different solvent is used in stage (a) and in stage (b), it is necessary to eliminate the solvent from the reaction mixture of stage (a) before carrying out stage (b). For example, it can be distilled.

It is also possible to carry out stage (a) and stage (b) in the same solvent. In this case, stage (a) is carried out in the anhydrous solvent and the nucleophilic reagent is added for carrying out stage (b).

Compound I can be separated by any known separating means, for example, the product according to formula I can be extracted by a chlorinated solvent such as chloroform, and the compound corresponding to formula I can then be separated from the chloroform phase by preparative chromatography.

Separation generally allows a by-product to be obtained which, by reduction, gives a compound corresponding to formula III indicated below, which can be recycled.

The compounds corresponding to formula II are known (see the above-mentioned Patents) or can be obtained from compounds corresponding to formula III

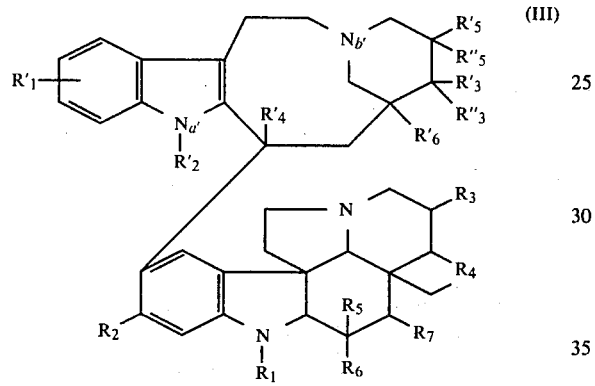

by processes known in this field, in particular by oxidation, for example, with the aid of perbenzoic acids in a solvent, in particular m-chloroperbenzoic acid in chloroform or in methylene chloride.

The compounds corresponding to formula III are known or can be prepared by the processes described in the above-mentioned Patents.

Process A

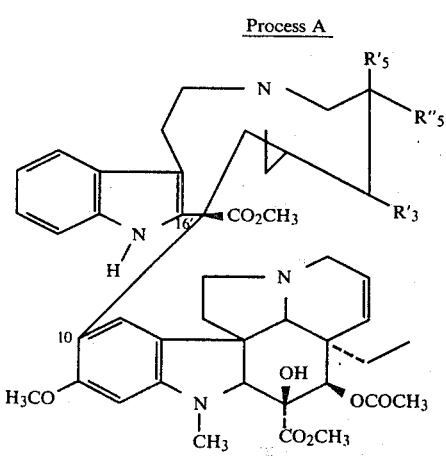

IIIa: $R'_5 = C_2H_5$; $R''_5 + R'_3 =$ double bond
IIIb: $R'_5 = C_2H_5$; $R''_5 = R'_3 = H$ -continued Process A

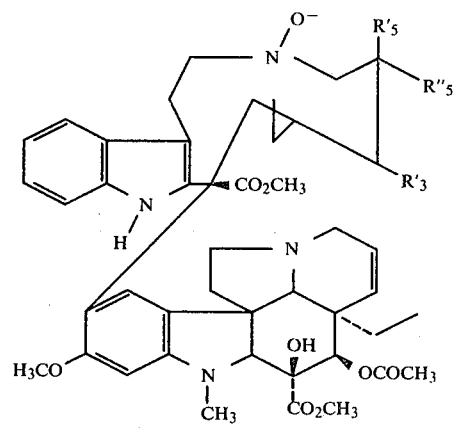

IIa: $R'_5 = C_2H_5$; $R''_5 + R'_3 =$ double bond
IIb: $R'_5 = C_2H_5$; $R''_5 = R'_3 = H$

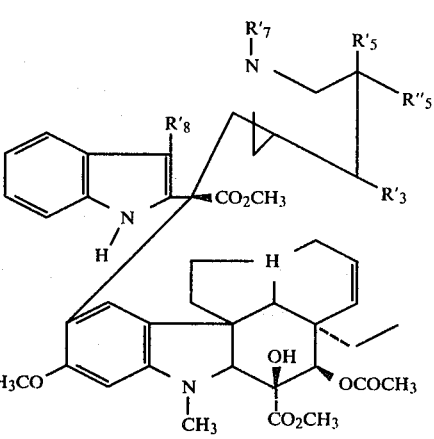

Ia1: $R'_5 = C_2H_5$; $R''_5 + R'_3 =$ double bond;
$R'_7 = CH_2CN$; $R'_8 = CH_2OCH_3$;
Ia2: $R'_5 = C_2H_5$; $R''_5 + R'_3 =$ double bond;
$R'_7 = CH_3$; $R'_8 = CH_3$;
Ia3: $R'_5 = C_2H_5$; $R''_5 + R'_3 =$ double bond;
$R'_7 = CH_3$; $R'_8 = CH_2OCH_3$;
Ia4: $R'_5 = C_2H_5$; $R''_5 = R'_3 = H$; $R'_7 = CH_2CN$;
$R'_8 = CH_2OCH_3$;
Ia5: $R'_5 = C_2H_5$; $R''_5 = R'_3 = H$; $R'_7 = H$;
$R'_8 = CH_2CH$.

The present invention also relates to a process B for the preparation of compounds corresponding to formula I, characterised in that a compound corresponding to general formula IV

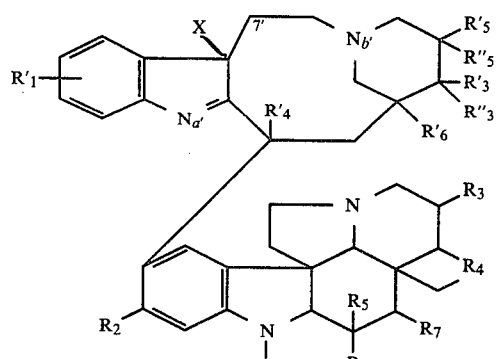

in which the substituents have the meaning given above and X represents a halogen, a hydroxy, hydroperoxy or alkanyloxy radical is reacted with one or more nucleophilic reagents, and the reaction can be carried out in a solution of water or in an inorganic solvent.

The process according to the present invention can be carried out without a catalyst, but the reaction can be catalysed by $Ag^+$ ions originating from silver salts such as silver perchlorate, tetrafluoroborate, trifluoroacetate or acetate, or an acidic reagent, for example, an inorganic acid such as hydrochloric acid.

The solvent used can be an organic solvent in the presence or absence of water. Suitable organic solvents include methanol, ethanol, tetrahydrofuran, chloroform, dichloromethane, dioxan, dimethylformamide, dimethylsulphoxide, hexamethylphosphotriamide or acetonitrile, chloroform or dichloromethane.

The reaction temperature is preferably between 0° C. and 100° C.

The nucleophilic reagent used can be selected from among the hydride ions obtained by the action of an alkaline borohydride, cyanide ions, thiolate, thiophenate or phenate ions, an amine, an alcohol or ammonia. The solvent itself can be the nucleophilic reagent, such as methanol or ethanol.

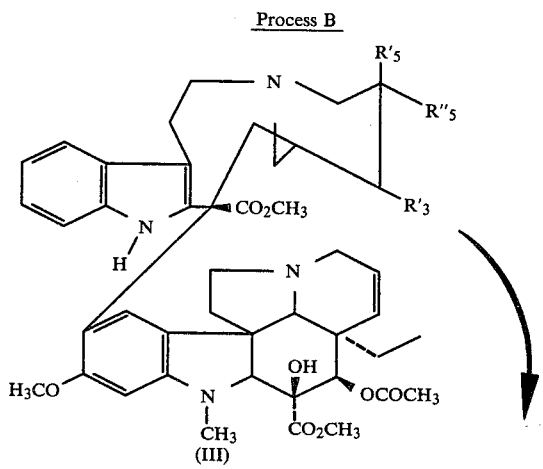

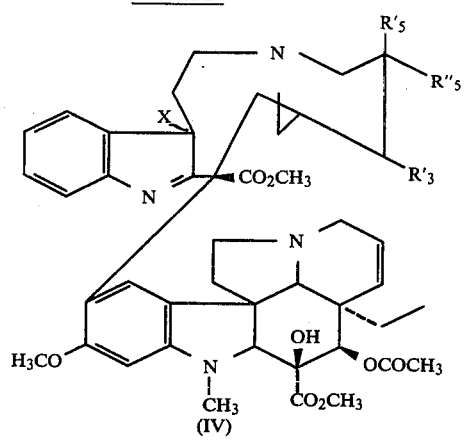

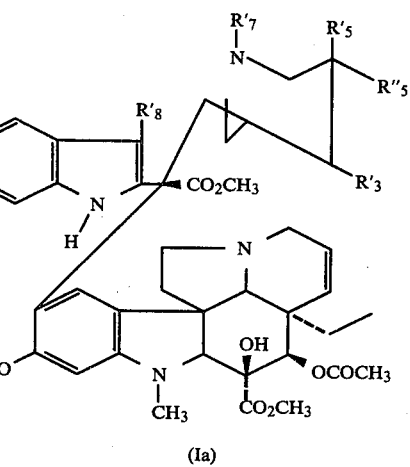

The compound I can be separated as in process A.

The compounds corresponding to formula IV are known (French Pat. No. 79 02981) and can be obtained from compounds corresponding to formula III which are themselves described in the above-mentioned Patents.

Other features for carrying out process A and process B according to the present invention can be deduced from the following Examples:

EXAMPLE 1

Preparation of the $N_{b'}$ oxide of $\Delta 15'$ 20'-deshydroxyvincaleucoblastine (IIa) (anhydrovinblastine)

180 mg (1.04 mmole) of metachloro-perbenzoic acid are added all at once to a solution of $\Delta 15'$ 20'-deshydroxy-vincaleucoblastine (IIIa) (748 mg; 0.94 mmole) in 10 ml of methylene chloride at 0° C. with stirring and under argon. The materials are left in contact for 30 minutes at 0° C. The reaction medium is then taken up in 100 ml of chloroform and the organic phase is washed four times with 3 ml of an aqueous solution of 40 g/l of sodium bicarbonate. The organic phase is then washed until neutral by water saturated with sodium chloride (3 times 10 ml), dried by sodium sulphate, filtered and evaporated under vacuum to yield 712 mg of the $N_{b'}$ oxide of $\Delta 15'$ 20'-deshydroxy-vincaleucoblastine (yield: 93%). U.V. ($\lambda$nm, $\epsilon$): 213, 268, 289, 293, 310. RMN$^1$H (400 MHz; $\delta$=0 ppm. TMS; J: Hz) 9.50 (s, 1H, $C_{16}$—OH); 8.19 (s, 1H, $N_a'$-H); 7.70 (d, 1H, J≈7.5, $C_9$-H or $C_{12'}$-H); 7.19 and 7.14 ($C_{10'}$-H and $C_{11'}$-H); 7.07 (d, J≈7.5, $C_{12'}$-H or $C_{9'}$-H); 6.43 (s, 1H, $C_9$-H); 6.11 (s, 1H, $C_{12}$-H); 5.84 (dd, 1H, $J_{14,15}$≈10 Hz and $J_{3,14}$≈4.5, $C_{14}$-H); 5.44 (1H, $C_{15'}$-H); 5.41 (s, 1H, $C_{17}$-H); 5.27 (d, 1H, $J_{14,15}$≈10 Hz, $C_{15}$-H); 4.51 (m, 2H); 4.32 (d, 1H) and 3.98 (d, 1H, $N_{b'}$-CH); 3.84 (s, 3H); 3.78 (s, 3H) and 3.69 (s, 3H, $C_{11}$-OCH$_3$, $C_{16}$CO$_2$CH$_3$ and $C_{16'}$CO$_2$CH$_3$); 2.62 (s, 3H, $N_a$-CH$_3$); 2.09 (s, 3H, OCOCH$_3$); 1.06 (t, 3H, $J_{18',19'}$=7 Hz, $C_{18'}$-H and 0.64 (t, 3H, $J_{18,19}$≈7 Hz, $C_{18}$-H). S.M.: 808, 806, 792, (M-16), 777, 761, 733, 669, 633, 631, 612, 611, 610, 510, 469, 282, 222, 200, 193, 144, 136, 135, 122, 121 (basic peak), 108, 107.

Preparation of
5',6'-seco-5'-cyano-6'-methoxy-anhydrovinblastine Ia1

The $N_{b'}$-oxide of anhydrovinblastine IIa (145 mg; 0.18 mmole) in solution in dry dichloromethane is treated for one hour under argon with trifluoro-acetic anhydride (0.12 ml; 0.83 mmole). After evaporation of the solvent without heating, the residue is dissolved in a saturated solution of potassium cyanide in methanol. This solution is stirred for two hours at 20° C., poured into an aqueous solution saturated with sodium chloride and extracted using chloroform (three times 50 ml). After drying over sodium sulphate, filtration and evaporation under vacuum of the chloroform solution, the dry residue is purified by preparative chromatography on a plate (eluant: CHCI$_3$-MeOH:93-7) and the compound Ia1 is obtained (82 mg, 54%).

Compound Ia1: $[\alpha]_D^{20}$=+7° (EtOH, C=0.6). IR: 3411, 2960, 1740, 1620. UV: 222(37000), 264(11200), 296(8000), 318 sh (5600). SM m/e: 863 (M$^+$.+14), 849 (M$^+$.), 819, 817, 790, 658, 656, 598, 379, 282, 258, 244, 222, 161, 135, 122, 121, 10 RMN (240 MHz): 7.61 and 7.37 (d, J=7 and d, J=7.5, 2H, aromatic indolic H), 7.14 (m, 2H, aromatic indolic H), 7.12 and 5.97 (2s, 2H, $C_9$-H and $C_{12}$-H), 5.91 (dd, $J_{14,15}$=9.5, $J_{3,14}$=3.5, 1H, $C_{14}$-H), 5.58 (s, 1H, $C_{17}$-H), 5.40 (d, $J_{14,15}$ 9.5, 1H, $C_{15}$-H), 4.87 (m, 1H, $C_{15'}$-H), 4.29 and 4.19 (2d, $J_{6'a,6'b}$=12, 2H, $C_{6'}$-H$_2$), 3.75, 3.61 and 3.36 (3s, 9H, $C_{11}$-OCH$_3$ $C_{16}$CO$_2$CH$_3$ and $C_{16'}$CO$_2$CH$_3$), 3.07 (s, 3H, CH$_2$-OCH$_3$), 0.84 and 0.76 (2t, 6H, $C_{18}$-H$_3$ and $C_{18'}$-H$_3$).

EXAMPLE 2

Preparation of 5',6'-seco-anhydrovinblastine Ia2:

The $N_{b'}$ oxide of anhydrovinblastine IIa (98 mg; 0.12 mmole) in solution in dry dichloromethane is treated for one hour at 0° C. and under argon with trifluoroacetic anhydride (0.08 ml; 0.5 mmole). After evaporation of the solvent without heating and under vacuum, the residue is dissolved in methanol (2 ml) and reduced with sodium cyanoborohydride (7 mg) for 30 minutes. After treatment as above, the residue is purified by preparative plate chromatography (eluant: CHCI$_3$-MeOH: 90-10). The anhydrovinblastine IIIa (24 mg; 24%) and the compound Ia2 (33 mg; 35%) are isolated.

Compound Ia2: $[\alpha]_D^{20}$=+19° (EtOH, C=0,5). IR=3460, 2960, 1740, 1610. UV: 218(13000), 263(5980), 288(4700), 296(4700). DC: 248 (+), 215 (+), 200 (−). SM m/e: 808, 794 (M$^+$.), 735, 657, 635, 598, 527, 282, 188, 152, 135, 122. RMN (240 MHz): 7.41 and 7.29 (2d, J=7,5, 2H, aromatic indolic H), 7.06 (m, 2H, aromatic indolic H), 6.90 and 6.00 (2s, 2H, $C_9$-H and $C_{12}$-H), 5,85 (dd, $J_{14,15}$=9.5 and $J_{3,14}$=3.5, 1H, $C_{14}$-H), 5.46 (s, 1H, $C_{17}$-H), 5.32 (d, $J_{14,15}$=9.5, 1H, $C_{15}$-H), 4.90 (s, large, 1H, $C_{15'}$-H), 3.76, 3.61 and 3.53 (s, 9H, $C_{11}$-OCH$_3$, $C_{16}$CO$_2$CH$_3$ and $C_{16'}$CO$_2$CH$_3$), 2.66 (s, 3H, $N_a$-CH$_3$) 2.24 (s, 3H, $N_{b'}$-CH$_3$), 2.08 (s, 3H, OCOCH$_3$), 1.95 (s, 3H, $C_{7'}$-CH$_3$), 0.87 and 0.63 (2t, $J_{18'19}$=7,5, 6H, $C_{18'}$-H$_3$ and $C_{18}$-H$_3$).

EXAMPLE 3

Preparation of
5',6'-seco-6'-methoxy-anhydrovinblastine Ia3

The $N_{b'}$ oxide of anhydrovinblastine IIa is treated as for the preparation of compound of Ia2 and reduced by an excess of sodium borohydride in methanol. After treatment as above and purification by preparative plate chromatography (eluant: CHCl$_3$-MeOH: 90-10), the compound Ia3 (30%) and anhydrovinblastine IIIa (25%) are obtained.

Compound Ia3: $[\alpha]_D^{20}$=−7.3° (EtOH, C=0.6). IR: 3405, 2950, 1745, 1620, UV: 220(37100), 263(11400), 284(9100), 292(8500), 314(5700). DC: 257 (+), 215 (+), 200 (−). SM m/e: 838, 824, (M$^+$.) 808, 794, 793, 792, 748, 734, 656, 598, (100%), 336, 282, 152, 135, 122. RMN (240 MHz) 7.41 and 7.29 (2d, J=7.5, 2H, aromatic indolic H), 7.03 (m, 2H, aromatic indolic H), 6.98 and 6.00 (2s, 2H, $C_9$-H and $C_{12}$-H), 5.90 (dd, $J_{14,15}$=9.5 and $J_{3,14}$=3.5, 1H, $C_{14}$-H) 5.54 (s, 1H, $C_{17}$-H), 5.40 (d, $J_{14,15}$=9.5, 1H, $C_{15}$-H), 5.02 (s, large, 1H, $C_{15'}$-H), 4.39 (dd, $J_{6'a,6'b}$=11, 2H, $C_{6'}$-H$_2$) 3.75, 3.62 and 3.48 (3s, 9H, $C_{11}$-OCH$_3$, $C_{16}$CO$_2$CH$_3$ and $C_{16'}$ C$_2$ CH$_3$), 3.10 (s, 3H, $C_{6'}$-OCH$_3$), 2.71 (s, 3H, $N_a$-CH$_3$), 2.38 (s, 3H, $N_{b'}$-CH$_3$), 2.16 (s, 3H, OCOCH$_3$), 0.98 and 0.85 (2t, $J_{18,19}$=7.5, 6H, $C_{18'}$-H$_3$ and $C_{18}$-H$_3$).

EXAMPLE 4

Preparation of the $N_{b'}$ oxide of 20'-desoxy-leurosidine IIb p-Nitro perbenzoic acid (13 mg; 0.07 mmole) is added to a solution of 20'-desoxy-leurosidine IIIb (45 mg; 0.056 mmole) in dry dichloromethane (1 ml) at 0° C. After ten minutes, the reaction medium is taken up in an aqueous solution of Na$_2$CO$_3$ (1 ml; C=40 g/l) and extracted three times using chloroform. After treatment as above and purification by preparative plate chromatography (eluant: CHCI$_3$-MeOH: 90-10), the $N_{b'}$ oxide of 20'-desoxyleurosidine is isolated (38 mg; 83%).

UV: 228, 268, 286, 296, 312. SM m/e: 822, 808, 794, 792, 612, 610, 468, 282, 138, 135 (100%), 124, 122, 121. RMN (60 MHz): 9.5 (s, 1H, $C_{16}$-OH), 7.9 (s large, 1H, $N_a'$-H) 7.3–6.8 (m, aromatic 4H), 6.3 and 6.0 (2s, 2H, $C_9$-H and $C_{12}$-H), 5,6 (m, 1H, $C_{14}$-H), 5,3 (s+m, 2H, $C_{17}$-H and $C_{15'}$-H), 3.7 and 3.5 (2s, 9H, OCH$_3$, $C_{16}$-CO$_2$CH$_3$ and $C_{16'}$-CO$_2$CH$_3$), 2.7 (s, 3H, $N_a$-CH$_3$), 2.0 (s, 3H, OCOCH$_3$), 0.8 (m, 6H, $C_{18}$-H$_3$ and $C_{18'}$-H$_3$).

Preparation of
5',6'-seco-5'-cyano-6'-methoxy-20'-desoxyleurosidine Ia4

The $N_{b'}$ oxide of 20'-desoxy-leurosidine (37 mg; 0.045 mmole) in solution in dry dichloromethane (0.6 ml) is treated with trifluoroacetic anhydride (0.03 ml; 0.21 mmole) at 0° C. under argon. After one hour, the reaction medium is evaporated under vacuum and dissolved in anhydrous methanol (2.5 ml). The potassium cyanide (25 mg) is added to this solution at 0° C. After 30', the reaction medium is taken up in water and extracted by chloroform. After conventional treatment, the residue (38 mg) is purified by preparative plate chromatography (eluant; CHCl$_3$MeOH: 93-7) and compound Ia4 is isolated (19 mg; 51%).

IR: 3300, 2950, 2300, 1740. UV: 220(58000), 264(11800), 284(9900), 295(9100), 315(sh 6000). DC: 295 (−3.8 285 (−3.8), 255 (+15.2), 228 (+9.5), 205 (−22.8). RMN (60 MHz): 9.8 (s large, $N_{a'}$-H or OH), 7.2–7.0 (m, aromatic 5H), 6.0 (s, 1H, $C_9$-H or $C_{12}$-H), 5.5 (s, 1H, $C_{17}$-H), 5.4 (s, 1H, $C_{15}$-H), 4.2 (s large, 2H, $C_{5'}$-H or $C_{6'}$-H), 3.8, 3.65, 3.45, 3.05 (4s, 12H, OCH$_3$, $C_{16}$-CO$_2$CH$_3$, $C_{16}$,CO$_2$CH, $C_{6'}$-OCH$_3$), 2.65 (s, 3H, $N_a$-CH$_3$), 2.05 (s, 3H, OCOCH$_3$), 0.65 (m, 6H, $C_{18}$-H$_3$ and $C_{18'}$-H$_3$). SM m/e: 851 (M+·), 821, 819, 690, 660, 282, (100%), 222, 163 (100%), 138 (100%), 136, 135 (100%), 124, 122, 121.

EXAMPLE 5

Preparation of R',6'-seco-5'-demethyl-6'-hydroxy-20'-deoxy leurosidine Ia5

Trifluoroacetic anhydride (0.065 ml; 0.45 mmole) is added to a solution of the $N_b$, oxide of 20'-desoxy-leurosidine (70 mg; 0.09 mmole) in dry dichloromethane (0.67 ml) with stirring and under argon. After one hour, the reaction medium is evaporated under vacuum and the residue is dissolved in tetrahydrofuran (5 ml). An aqueous solution of Na$_2$ CO$_3$ (40 g/l; 0.012 ml) is added and the reaction medium is stirred for over night at ordinary temperature. After extraction using CHCl$_3$ and conventional treatment, the residue is purified by preparative plate chromatography (eluant:CHCl$_3$-MeOH:90-10), and the compound Ia5 is isolated (16 mg; 23%).

IR: 3400, 2950, 1740. UV: 222(50000), 265(14000), 285(12000), 292(11200), 310(sh 7000). DC: 295 (−4.0), 287 (−4.0), 260 (+18.3), 225 (+16.6), 215 (−18.0). SM m/e: 810, 796, 794, 764, 750, 738, 736, 598, 577, 522, 480, 282, 144, 138 (100%), 135 (100%, 125, 124 (100%), 122, 121. RMN (250 MHz): 8.70 (s, 1H, $N_{a'}$-H or OH), 7.55–7.0 (m, aromatic 4H), 7.02 and 5.97 (2s, 2H, $C_9$-H and $C_{12}$-H), 5.91 (m, 1H, $C_{14}$-H), 5.49 (s, 1H, $C_{17}$-H), 5.34 (d, $J_{14,15}$=7.5, 1H, $C_{15}$-H), 4.28 (s large, 2H, $C_{6'}$-H), 3.79, 3.66, 3.42 (3s, 9H, OCH$_3$, $C_{16}$CO$_2$CH$_3$, $C_{16}$,CO$_2$CH$_3$), 2.70 (s, 3H, $N_a$-CH$_3$), 2.12 (s, 3H, OCOCH$_3$), 0.70 and 0.52 (2t, 6H, J=7, $C_{18}$-H$_3$ and $C_{18'}$-H$_3$)

EXAMPLE 6

Preparation of 5',6'-seco-6'-methoxy-anhydrovinblastine (Process B)

18 mg of AgBF$_4$ are added to a solution of 66 mg (0.08 mmole) of the 7'-chloro indolenine of anhydrovinblastine prepared in the manner described in Patent No. 79 02981 (6.02.79) (1st Certificate of addition to Patent Application No. 78 24568 (of 24.08.78)) in 7 cm$^3$ of anhydrous THF and the mixture is stirred at 40° C. for five hours. The solvent is removed by evaporation under reduced pressure. After addition of 2 cm$^3$ of methanol and reduction by an excess of sodium borohydride and conventional treatments, 34 mg (50%) of the dimer Ia3 are isolated.

The compounds corresponding to formula I according to the present invention have anti-tumoral properties and can therefore be used in the treatment of various tumoral infections such as leukemia.

The present invention also relates to the compounds corresponding to formula I as well as the pharmaceutical compositions containing them, as new drugs.

The results of pharmacological investigations carried out in vitro and in vivo on the compound from the Examples are given below.

Inhibition of polymerisation of tubuline

Tubuline is the receiver of anti-tumoral indolic alkaloids of the vinblastine type.

It is easily extracted from pigs' brains where it represents 10% of the soluble proteins.

Polymerisation of tubuline into microtubules can easily be followed by means of an ultraviolet spectrophotometer by observing at 350 nm. The maximum polymerisation rate is thus determined; it is reduced by the addition of inhibitors of the vinblastine type, and the concentration, $I_{50}$, which halves the rate is obtained for each substance tested. A second effect of these products is taken into consideration: at higher dosages, after total inhibition of polymerisation, spiralisation of the tubuline is observed (checked by electron microscopy) and a new concentration, $S_{50}$, corresponding to the appearance of 50% of the phenomenon is determined.

The results for each product are always compared to those of vinblastine used as a reference.

It has been found that the results obtained when adopting the above-mentioned experiments had a excellent correlation with the results obtained in the case of animal tumours. Thus, in the following table the compounds having $I_{50}$ or $S_{50}$ values of the order of $10^{-5}$ at least are of therapeutic interest.

Results:

| Compounds | $I_{50}$ mole/l | $S_{50}$ mole/l |
| --- | --- | --- |
| Vinblastine | $1.7 \times 10^{-6}$ | $9 \times 10^{-6}$ |
| Ia1 | $3.4 \times 10^{-6}$ | $4.5 \times 10^{-6}$ |
| Ia2 | $2.38 \times 10^{-4}$ | — |
| Ia3 | $5.1 \times 10^{-6}$ | $6.7 \times 10^{-6}$ |
| Ia4 | $6.4 \times 10^{-5}$ | — |
| Ia5 | $1.7 \times 10^{-5}$ | — |

The present invention also relates to pharmaceutical compositions containing a new compound corresponding to formula I or one of its salts, optionally in combination with any other pharmaceutically compatible product which can be inert or physiologically active.

These compositions can be presented in any form which is suitable for the proposed method of administration. The parenteral method of administration is preferred, particularly the intravenous method.

The compositions according to the invention for parenteral administration can be sterile aqueous or non-aqueous solutions, suspensions or emulsions. Propylene glycol, polyethylene glycol, vegetable oils, in particular olive oil, and injectable organic esters, in particular ethyl oleate, can be used as a solvent or medium. These compositions can also contain additives, in particular wetting agents, emulsifiers and dispersants. Sterilisation can be carried out in several ways, for example, by means of a bacteriological filter, by incorporating sterilising agents into the composition, by irradiation or by heating. They can also be prepared in the form of sterile solid compositions which can be dissolved or dispersed in sterile water or any other injectable sterile medium at the moment of use.

The new compounds or their salts are active in the treatment of solid or liquid tumours and, more particularly, human cancers, in daily dosages of between 10 and 20 mg per day for adults.

The following Example illustrates a composition according to the invention.

EXAMPLE

A solution containing 10 mg/cm³ of active substance is prepared by dissolving 1 g of the product Ia from the Example in 100 cm³ of an apyrogenic physiological aqueous solution. The solution obtained is distributed aseotically in ampoules of 2 cm³ in a proportion of 1 cm³ per ampoule. The ampoules are sealed and each contain 10 mg of active ingredient.

We claim:

1. Compounds corresponding to the general formula:

(I)

in which
$R'_1$ is selected from a hydrogen atom, formyl, and alkoxy, acyl, and halogenoacyl radicals of 1 to 5 carbon atoms, $R'_2$ is selected from a hydrogen atom and alkyl radicals of 1 to 5 carbon atoms, $R'_3$ and $R''_3$ are each independently selected from a hydrogen atom and hydroxyl and alkanoyloxy radicals of 1 to 5 carbon atoms, or $R'_3$ and $R''_3$ together form a carbonyl group, or $R'_3$ and $R'_5$ together form an epoxy bridge or a double bond, $R'_4$ is selected from a hydrogen atom and alkyloxycarbonyl in which the alkyl portion has from 1 to 5 carbon atoms, hydroxymethyl, alkanoyloxymethyl radicals in which the alkanoyloxy portion has from 1 to 5 carbon atoms and acetamido radicals, $R'_5$ and $R''_5$ are each independently selected from a hydrogen atom and hydroxyl, alkanoyloxy radicals of 1 to 5 carbon atoms, ethyl and 2-hydroxyethyl radicals, $R'_6$ is selected from a hydrogen atom and ethyl, 2-hydroxyethyl and acetyl radicals, $R'_7$ and $R'_8$ are each independently selected from a hydrogen atom and methyl, hydroxymethylene, alkoxymethylene in which the alkoxy group has 1 to 5 carbon atoms, aryloxymethylene in which the aryl group is monocyclic with 5 or 6 atoms in the ring, aminomethylene, monoalkyl and dialkyl aminomethylene in which the alkyl groups have from 1 to 5 carbon atoms, arylaminomethylene in which the aryl group is monocyclic with 5 or 6 atoms in the ring, hydroxyethyl aminomethylene, alkyl thiomethylene in which the alkyl group has from 1 to 5 carbon atoms, aryl thiomethylene in which the aryl group is monocyclic and has 5 or 6 atoms in the ring, cyanomethylene and acylmethylene radicals in which the acyl portion has from 1 to 5 carbon atoms, $R_1$ is selected from a hydrogen atom and alkyl, formyl and acyl radicals in which the alkyl and acyl radicals have from 1 to 5 carbon atoms, $R_2$ is selected from a hydrogen atom and alkoxy radicals having from 1 to 5 carbon atoms, $R_3$ is selected from a hydrogen atom and hydroxyl and alkanoyloxy radicals of 1 to 5 carbon atoms, or $R_3$ and $R_4$ together form an epoxy bridge or a double bond, $R_4$ is selected from a hydrogen atom and hydroxyl and alkanoyloxy radicals of 1 to 5 carbon atoms or $R_4$ and $R_5$ together form an epoxy bridge, $R_6$ is selected from alkyloxycarbonyl in which the alkyl portion has from 1 to 5 carbon atoms, hydrazido, acetamido, hydroxymethyl and alkanoyloxymethylene radicals in which the alkanoyloxy portion has 1 to 5 carbon atoms, $R_5$ and $R_7$ are selected from a hydrogen atom and hydroxide and alkanoyloxy radicals of 1 to 5 carbon atoms, as well as their pharmaceutically acceptable acid addition salts and their pharmaceutically acceptable quaternary ammonium salts.

2. Compounds according to claim 1 corresponding to formula Ia:

(Ia)

in which:
$R'_3$ is selected from a hydrogen atom and a hydroxy radical, $R'_5$ is selected from a hydrogen atom and a hydroxy radical, or $R'_3$ and $R'_5$ together represent an epoxy bridge or a double bond, $R''_5$ is selected from a hydrogen atom and an ethyl radical, $R'_7$ and $R'_8$ are each independently selected from a hydrogen atom and methyl, hydroxymethylene, alkoxymethylene in which the alkoxy portion has 1 to 5 carbon atoms, aryloxymethylene in which the aryl group is monocyclic and has 5 or 6 atoms in the ring, aminomethylene, monoalkyl or dialkylaminomethylene in which the alkyl portions thereof have 1 to 5 carbon atoms, acylmethylene in which the acyl portion thereof has 1 to 5 carbon atoms, arylaminomethylene in which the aryl group is monocyclic and has 5 or 6 atoms in the ring, hydroxyethyl aminomethylene, alkyl thiomethylene in which the alkyl portion has 1 to 5 carbon atoms, aryl thiomethylene in which the aryl group is monocyclic and has 5 or 6 atoms in the ring and cyanomethylene radicals, $R_1$ is selected from a hydrogen atom and alkyl, formyl and acyl radicals in which said alkyl and acyl radicals have 1 to 5 carbon atoms, $R_2$ is selected from a hydrogen atom and alkoxy radicals of 1 to 5 carbon atoms, $R_7$ represents an alkanoyloxy radical of 1 to 5 carbon atoms, the broken line representing an optional double bond, as well as the corresponding pharmaceutically acceptable salts.

3. The compounds corresponding to formula Ia in claim 2 wherein the compounds are:

5',6'-seco-5'-cyano-6'-methoxy-anhydrovinblastine,
5',6'-seco-anhydrovinblastine,
5',6'-seco-6'-methoxy-anhydrovinblastine,
5',6'-seco-5'-cyano-6'-methoxy-20'-deoxy-leurosidine, or
5',6'-seco-5'-demethyl-6'-hydroxy-20'-deoxy-leurosidine.

4. A process for the preparation of the compounds according to claim 1, which comprises:

(a) reacting a compound corresponding to Formula II:

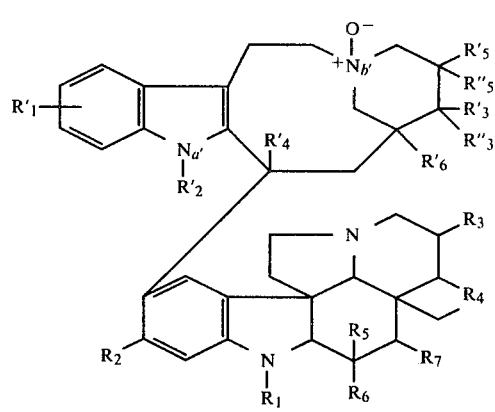

in which the substituents have the meaning given above, in the presence of an immonium ion-forming reagent selected from the group consisting halides, anhydrides and salts of organic or inorganic acids, and (b) treating the product obtained with at least one nucleophilic reagent selected from the group consisting of an alcohol, a phenol, a thiol, an amine, a carboxylic acid, a cyanide ion, a hydride ion and ammonia, and separating the compound corresponding to Formula I.

5. A process according to claim 4, wherein the immonium ion-forming reagent is selected from halides or anhydrides of halogenated carboxylic acid salts.

6. A process according to claim 5, wherein the immonium ion-forming reagent is trifluoracetic anhydride.

7. A process according to claim 4 wherein stage (a) is carried out in an anhydrous organic solvent.

8. A process according to claim 7, wherein the anhydrous organic solvent is a chlorinated organic solvent.

9. A process according to claim 8, wherein the chlorinated solvent is methylene chloride, dichloroethane or chloroform.

10. A process according to claim 4, wherein stage (a) is carried out at a temperature of between $-5°$ C. and $+5°$ C.

11. A process according to claim 4, wherein stage (b) is carried out by treating the product from stage (a) with a mixture of organic solvent and water.

12. A process according to claim 11, wherein the organic solvent is a nucleophilic reagent selected from the group consisting of an alcohol, a phenol, a thiol, an amine, a carboxylic acid, a cyanide ion, a hydride ion and ammonia.

13. A process according to claim 4, wherein the reaction mixture from stage (a) is dried before stage (b).

14. A process according to claim 4, wherein the compound of formula I is separated from the reaction mixture from stage (b) by extraction using a chlorinated solvent and chromatography.

15. A process for the preparation of the compounds according to any one of claims 1 to 3, which comprises reacting a compound corresponding to Formula IV:

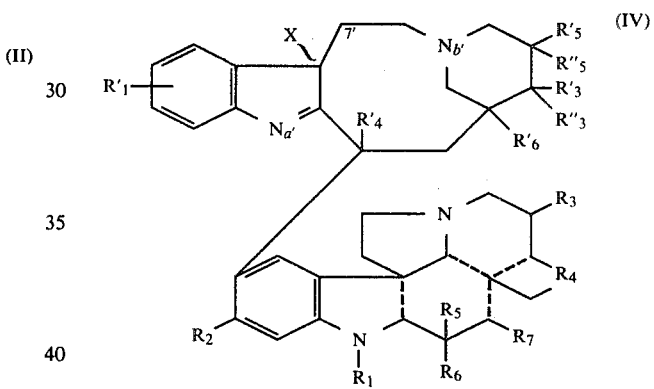

in which the substituents have the meaning given above and X is selected from a halogen, a hydroxy, hydroperoxy and alkanoyloxy radical of 1 to 5 carbon atoms, in the presence of a nucleophilic reagent selected from the group consisting of an alcohol, a phenol, a thiol, an amine, a carboxylic acid, a cyanide ion, a hydride ion and ammonia.

16. A process according to claim 15 wherein the reaction is concluded in the presence of an organic solvent selected from the group consisting of methanol, ethanol, chloroform, dichloromethane, tetrahydrofuran, dioxan, dimethylformamide, dimethylsulphoxide, hexamethylphosphorotriamide and acetonitrile.

17. A pharmaceutical composition for treating leukemia comprising an effective amount of at least one compound according to any one of claim 1 to 3 as active ingredient.

18. A method of treating leukemia comprising administering an effective amount of a compound according to claim 1.

* * * * *